(12) United States Patent
McLaren et al.

(10) Patent No.: US 9,861,654 B2
(45) Date of Patent: Jan. 9, 2018

(54) TREATMENT OF DIARRHEA AND POST-WEANING DIARRHEA WITH RESISTANT POTATO STARCH

(71) Applicant: MCPHARMA BIOTECH INC., Carberry (CA)

(72) Inventors: Derek McLaren, Carberry (CA); Earl McClaren, Carberry (CA)

( * ) Notice: Subject to any disclaimer, the term of this patent is extended or adjusted under 35 U.S.C. 154(b) by 42 days.

(21) Appl. No.: 14/426,253

(22) PCT Filed: Sep. 6, 2013

(86) PCT No.: PCT/CA2013/050689
§ 371 (c)(1),
(2) Date: Mar. 5, 2015

(87) PCT Pub. No.: WO2014/036655
PCT Pub. Date: Mar. 13, 2014

(65) Prior Publication Data
US 2015/0250814 A1     Sep. 10, 2015

Related U.S. Application Data

(60) Provisional application No. 61/697,440, filed on Sep. 6, 2012.

(51) Int. Cl.
| | |
|---|---|
| *A23K 1/18* | (2006.01) |
| *A61K 31/718* | (2006.01) |
| *A61K 36/81* | (2006.01) |
| *A61K 9/20* | (2006.01) |
| *A23K 40/10* | (2016.01) |
| *A23K 40/30* | (2016.01) |
| *A23K 10/35* | (2016.01) |
| *A23K 20/163* | (2016.01) |
| *A23K 50/10* | (2016.01) |
| *A23K 50/30* | (2016.01) |
| *A23K 50/60* | (2016.01) |

(52) U.S. Cl.
CPC ............ *A61K 31/718* (2013.01); *A23K 10/35* (2016.05); *A23K 20/163* (2016.05); *A23K 40/10* (2016.05); *A23K 40/30* (2016.05); *A23K 50/10* (2016.05); *A23K 50/30* (2016.05); *A23K 50/60* (2016.05); *A61K 9/2027* (2013.01); *A61K 9/2059* (2013.01); *A61K 36/81* (2013.01); *A23V 2002/00* (2013.01)

(58) Field of Classification Search
None
See application file for complete search history.

(56) References Cited

U.S. PATENT DOCUMENTS

2004/0137038 A1*    7/2004    Brown .................. A21D 2/186
                                                           424/442

FOREIGN PATENT DOCUMENTS

WO       WO 9015147 A1 * 12/1990  ............. A23L 1/095

OTHER PUBLICATIONS

Bhandari, J. Anim. Sci. 2009, 87:984-993.*
Hausmanns, DE 10244359 A1, Apr. 2004, machine translation.*
M.S. Hedemann et al "Resistant starch for weaning pigs"Effect on Concentration of short chain fatty acids in digesta and intestinal Morphology: livestock science 2007,108p;p. 175-77.
D.O. Krause et al "response of nursery pigs to a synbiotic preparation of starch and an anti-*Escherichia coli* K88 probiotic" Applied and Environmental . . . Microbiology 2010 76 (242)pp. 8291-8200.
J. Yu "Substitute breast milk useful for piglets for stimulating immunity, comprises hydrolyzed soybean protein, wheat protein concentrate, . . . potatio starch, water soluble fat powder, glucose, fructose, oligosaccharide, lysine, and threonine" 2009, 4 XP002657927.
R. Pieper et al "Influence of different carbohydrate composition in barley varieties on *Salmonella typhimurium* var. Copenhagen colonization in a . . . "Trojan" challenge model in pigs:", Archives of Animal nutritiion, 2012,66 (3), pp. 163-179.
L. Xue "Use of Fermented Potato Pulp in 1-8 Diets Fed to Lactating Sows" journal of animal and veterinary advances, 2011 pp. 2032-2037.
R. Pieper et al "Influence of different carbohydrate composition in barley varieites on *Salmonella typhimurium* var. Copenhagen colonization in a "Trojan" . . . challenge model in pigs" archives of animal nutrition 2012 66 (3) pp. 163-179.

* cited by examiner

*Primary Examiner* — Layla D Berry
(74) *Attorney, Agent, or Firm* — Michael R. Williams; Ryan W. Dupuis; Ade & Company Inc.

(57) ABSTRACT

Low levels of resistant potato starch, for example, 0.5-1.0% of total diet, have a beneficial effect on post-weaning diarrhea, infectious diarrhea and gastrointestinal stresses associated with weaning. Also described are capsules and tablets of resistant potato starch, and methods for making said capsules and tablets.

14 Claims, No Drawings

TREATMENT OF DIARRHEA AND POST-WEANING DIARRHEA WITH RESISTANT POTATO STARCH

PRIOR APPLICATION INFORMATION

The instant application claims the benefit of U.S. Provisional Patent Application 61/697,440, filed Sep. 6, 2012.

BACKGROUND OF THE INVENTION

Post-weaning diarrhea (PWD) is one of the major economic loses in the pig industry and is often caused by multiple factors, including nutritional, physiological, environmental and psychological stressors (Heo et al., 2012; Kim et al., 2012).

The most effective strategy to control weaning-associated diarrhea remains prophylactic and (or) therapeutic levels of antimicrobial compounds like zinc oxide (ZnO), copper sulphate ($CuSO_4$) and antibiotics in the feed. However, due to concerns regarding the development of antibiotic resistant strains in foodborne pathogens as well as environmental contamination, there is ongoing interest to minimize or completely eliminate the use of in-feed antibiotics in animals (Lusk et al., 2006).

One proposed alternative to ameliorate PWD and improve gut health of pigs is the use of prebiotics like resistant starch. A prebiotic has been defined as "a selectively fermented ingredient that allows specific changes, both in the composition and (or) activity of microbiota, that confer benefits upon host well-being and health" (Gibson et al., 2004). Resistant starch from potato (*Solanum tuberosum*) is such a prebiotic and a case can be made that resistant starch is a vital component of a healthy animal gut microbiome. As such, it can be demonstrated that resistant starch from potato aids in (i) establishment and promotion of beneficial gut microbes, including but not limited to phyla Actinobacteria, Bacteriodetes, Firmicutes and Proteobacteria; (ii) altered carbohydrate metabolism and insulin response in animals; (iii) increased uptake, absorption and transport of micro- and macronutrients; (iv) improved integrity of the gastrointestinal tract including mucosal lining (v) improvement in immune function including corresponding alteration of the pro- and anti-inflammatory milieu; and (vi) changes in fatty acid production and fatty metabolism.

Previous research conducted at the University of Manitoba reported that feeding weaned pigs a diet containing 7% resistant potato starch (RPS) resulted in reduced PWD without any adverse effects on growth performance. However, there were no differences in PWD and growth performance for piglets fed a 14% RPS diet compared with those fed the negative control diet.

Therefore, the purpose of this study was to determine the effects of dietary inclusion of low amounts of resistant potato starch on piglet growth performance and other indicators of gastrointestinal health.

SUMMARY OF THE INVENTION

According to one embodiment of the invention, there is provided a method of treating or preventing or prophylactically treating infectious diarrhea in an animal comprising administering to an animal in need of such treatment an effective amount of resistant potato starch.

According to one embodiment of the invention, there is provided a method of treating or preventing or prophylactically treating post-weaning diarrhea in an animal comprising administering to an animal in need of such treatment an effective amount of resistant potato starch.

According to one embodiment of the invention, there is provided a method of treating or preventing or prophylactically treating gastrointestinal stresses associated with weaning in an animal comprising administering to an animal in need of such treatment an effective amount of resistant potato starch.

In preferred embodiments, the resistant potato starch is MSPrebiotic® Resistant Starch (resistant potato starch for human health indications) or MSP[RS]® Resistant Starch (resistant potato starch for livestock industry use).

As will be readily apparent to one of skill in the art, "an effective amount" will depend on the animal, its age, weight and general condition, among other factors. However, as discussed above, the inventors have discovered that a much lower level of resistant starch than previously believed is sufficient to treat or otherwise ameliorate at least one of the symptoms associated with infectious diarrhea, post-weaning diarrhea and/or gastrointestinal stresses associated with weaning such as poor fecal consistency, reduced daily food intake and the like. For example, in some embodiments, the "effective amount" is resistant starch at approximately 0.3-2.5%. 0.3-2.0%, 0.3-1.5%, 0.3-1.0%, 0.4-2.5%, 0.4-2.0%, 0.4-1.5%, 0.4-1.0%, 0.5-2.5%. 0.5-2.0%, 0.5-1.5%, or 0.5-1.0% of the animal's diet.

In other embodiments, the "effective amount" may be a resistant potato starch capsule or tablet. The resistant starch capsule or tablet may be prepared according to the methods described herein. Preferably, the resistant potato starch capsule may be about 500 mg, while the tablet may be 250 mg. Preferably, the resistant potato starch capsule is MSPrebiotic® Resistant Starch or MSP[RS]® Resistant Starch.

According to another embodiment of the invention, there is provided the use of resistant potato starch for treating infectious diarrhea in an animal.

According to another embodiment of the invention, there is provided the use of resistant potato starch for treating post-weaning diarrhea in an animal.

According to another embodiment of the invention, there is provided the use of resistant potato starch for treating gastrointestinal stresses associated with weaning in an animal.

In yet another embodiment of the invention, there is provided a transitional food product for weaning animals comprising an effective amount of resistant potato starch.

As used herein, "transitional food" refers to a food fed to a weaning animal that is transitioning from primarily liquid feed to solid feed.

In one embodiment of the invention, there is provided a method of preparing a resistant potato starch pharmaceutical composition comprising mixing an effective amount of resistant potato starch with a suitable excipient.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As discussed above, post-weaning diarrhea is a serious problem for the livestock industry. As used herein, "livestock" can be considered to be any animal for example a farm animal kept for use or profit for example kept for domestic use and not as pets, especially on a farm or ranch. One such example is the pig industry; however a wide variety of animals including fish are now kept as livestock.

Post-weaning diarrhea is caused by nitrogen-utilizing or enterotoxigenic bacteria such as E. coli. As discussed above, this disease is caused by multiple factors: (i) cessation of passive transmission of maternal antibodies; (ii) change in feed, resulting in undigested food stuff being present in the digestive tract; (iii) additional stressors caused by separation from the mother and relocation and (iv) stresses caused by raising animals in a high density. For example, in the pig industry, on cessation of weaning, the piglets no longer have antibodies from the sow passively transmitted with the milk. Consequently, these piglets will lack antibodies against enterotoxigenic bacteria and are susceptible to infection by same.

As such, "weaning" in some cases can be considered to be a period in an animal's life during which the animal is fed primarily liquid feed. Post-weaning refers to the transition from liquid feed to solid feed. Transitional food refers to foods fed to a weaning animal during this time period. Post weaning, there will be an average of 20-40% of undigested protein substance available in the large intestine where it is fermented by the microbiota or gut microflora which can lead to over-growth of nitrogen-utilizing bacteria.

Post-weaning diarrhea in some animals known as "scours" and is often treated by administering antibiotics to the piglets. In many cases, the disease is treated prophylactically by administering antibiotics to all piglets which it is believed promotes gut health and results in more efficient processing of feed by the piglets, which is a key consideration in the pig industry. Specifically, it is believed that the antibiotics reduce the levels of the nitrogen-utilizing bacteria, allowing for increased growth of lactic acid bacteria such as Lactobacilli and Bifidobacteria However, concerns regarding the overuse of antibiotics and increased antibiotic resistance in pathogens has led to the search for alternatives to antibiotics.

One alternative is prebiotics, which typically promote growth of beneficial bacteria such as lactic acid bacteria and/or inhibit growth of pathogenic bacteria such as enterotoxigenic bacteria.

One such prebiotic is resistant starch. As will be appreciated by one of skill in the art, "resistant starch" as used herein refers to a starch which is composed of a high percentage of resistant starch. In some embodiments, the resistant starch is starch from a botanical source that is naturally high in resistant starch, that is, at least 60-80% resistant starch. As discussed below, in preferred embodiments, the resistant starch is resistant potato starch. Exemplary examples of such resistant potato starch are MSPrebiotic® Resistant Starch (resistant potato starch for human health indications) and MSP[RS]® Resistant Starch (resistant potato starch for livestock industry use). In yet more preferred embodiments, the resistant potato starch is MSPrebiotic® Resistant Starch (resistant potato starch for human health indications) or MSP[RS]® Resistant Starch (resistant potato starch for livestock industry use).

It is believed that one of the protective mechanisms of resistant starch is through short chain fatty acid (SCFA) production. Specifically, short chain fatty acids such as propionate and formate have been shown to kill E. coli or Salmonella at high acidity (pH 5). Alternatively, fermentation of resistant starch is also believed to promote the growth and activity of beneficial lactic acid bacteria and to alter the profile of the gut microflora.

Previous studies involving the feeding of resistant starch in animal models have used relatively high diet percentages of resistant starch, based on the belief that high levels of resistant starch were necessary in order to ensure that the desired effects were observed, such as production of sufficient short chain fatty acids and alteration of pH in compartments of the gastrointestinal tract. In addition, the fermentation of natural resistant starch reduces the intestinal pH and also reduces the production of potentially harmful secondary bile acids, ammonia and phenols. Consequently, it was widely believed that relatively high levels of resistant starch would be necessary in order to effect a noticeable change in fatty acid profile, microbiota composition and pH in the intestinal tract.

Specifically, it was previously demonstrated that pigs fed a diet comprising 7% resistant potato starch in fact consumed less feed than controls while pigs fed a diet comprising 14% resistant potato starch had increased feed consumption compared to controls (Bhandari et al., 2009). However, in both cases, growth was reduced compared to controls.

7% resistant potato starch did however improve fecal consistency, resulting in values similar to those obtained with a positive control treated with a sub-therapeutic amount of antibiotics. However, 14% resistant potato starch produced fecal consistency scores consistent with those of the untreated control, that is, pigs that were not fed resistant potato starch or administered any antibiotics and therefore were susceptible to post-weaning diarrhea.

As can be seen, while the 7% resistant potato starch improved fecal consistency (which means that the severity of PWD was reduced), it also reduced the growth rate of the pigs, either by promoting satiety so the pigs ate less or as a side-effect of the nutritional content of the feed being reduced as a result of such a large percentage of the feed being resistant potato starch. The authors concluded that while 7% resistant potato starch did not replace the growth-enhancing effects of sub-therapeutic antibiotics, it did reduce scours somewhat in the absence of the administration of antibiotics.

Furthermore, 14% resistant potato starch had no effect on fecal consistency, meaning that PWD severity was not reduced in this treatment group. Surprisingly, 14% resistant starch caused increased feed uptake, meaning that it was not promoting satiety; however, growth was still reduced, indicating that this treatment group was not able to efficiently process the feed consumed. Thus, the increase in feed intake did not translate into an improvement in weight gain or efficiency. This indicates that the greater concentration of dietary starch is in fact impairing digestion.

Consequently, based on these results, one of skill in the art would conclude that a diet including 7% resistant potato starch is suitable in cases of severe or widespread PWD in which there is a desire to avoid use of antibiotics. This would be anticipated to have a negative impact on growth rate, as discussed above, albeit not a significant one.

Furthermore, one would assume that 7% resistant potato starch would be difficult if not impossible to incorporate into a human diet to treat diseases analogous to PWD, such as infectious diarrhea in humans and difficulties associated with transition from breast milk or formula to solid foods in human infants. Simply put, it was previously believed that a diet consisting of 7% resistant potato starch would be difficult to achieve or maintain in humans.

For example, for even a 2000 calorie diet, an individual would have to consume 140 calories of resistant starch to meet the 7% level. Given that each gram of protein or carbohydrates such as starch has approximately 4 calories while each gram of fat has approximately 9 calories, which equates to approximately 35 grams of resistant starch for a 2000 calorie daily diet to reach 7%.

Furthermore, as discussed above, it was not believed that low doses of resistant starch would have sufficient effect (or any effect at all) on gut health or post-weaning diarrhea. Specifically, it was believed that a significant amount of resistant starch was necessary to alter the composition of the microbiota, lower the pH of the digestive tract and to decrease branched-chain fatty acid levels in favor of short chain fatty acids and/or volatile fatty acids. Specifically, it was assumed that at least 7% of the diet would have to be resistant starch for such effects to be observed or detected.

However, as discussed below, the inventors have surprisingly discovered that low levels of resistant potato starch, for example, 0.5% to 1.0% of a diet, still have a beneficial effect on PWD, infectious diarrhea and gastrointestinal stresses associated with weaning.

However, the botanical source of the resistant starch must be high in resistant starch and care must be taken during processing and/or preparation to ensure that losses of resistant starch due to gelatinization and/or fracturing of the resistant starch granule structure are minimized.

Preferably, the resistant starch is from a source that is naturally 60-80% resistant starch. That is, a botanical source that is naturally high in resistant starch, that is, at least 60-80% resistant starch. In some embodiments, the resistant starch source that is 60-80% resistant starch is resistant potato starch. In preferred embodiments, the resistant potato starch is MSPrebiotic® Resistant Starch or MSP[RS]® Resistant Starch.

The resistant starch may be prepared initially using any of a variety of means known in the art. In some embodiments, the resistant potato starch is a by-product of French fry or potato chip preparation or is prepared directly from potatoes grown specifically for starch. An exemplary example of such a resistant potato starch is MSPrebiotic® Resistant Starch or MSP[RS]® Resistant Starch.

In some embodiments, potatoes are washed prior to being subjected to an extraction process to remove starch granules from the cells. For example, high powered washing on rotating conical sleeves may be used to separate a starch-containing slurry from potato pulp. The crude starch slurry is then concentrated and refined.

As discussed below, a study was carried out to evaluate the effect of feeding weaned pigs a lower level of resistant starch, for example, resistant potato starch, specifically, a diet including 0.5-1.0% resistant potato starch. Surprisingly, while average daily feed intake and average daily gain were not significantly affected by the addition of the low amounts of resistant potato starch, fecal consistency was improved, consistent with treatment of post-weaning diarrhea, as discussed above.

As will be appreciated by one of skill in the art, for a 2000 calorie daily diet, an animal would need only to consume 10 or 20 calories of resistant starch which is only 2.5 or 5.0 grams, which is much more manageable.

Accordingly, the inventors then proceeded to investigate the development of pharmaceutical products.

As discussed herein, considerable care must be taken to ensure that as much of the resistant starch is retained as possible. As discussed below, the inventors have discovered that there are several additional considerations beyond maintaining a temperature below 60° C. when preparing pharmaceutical products such as tablets and capsules from resistant starch such as moisture content of the starch and pressure used in tablet formation.

Initially, the inventors attempted to develop resistant starch-containing capsules. However, initial attempts were unsuccessful as the resistant starch tended to clump together and was difficult to fill or flow into a suitably sized capsule. It was subsequently discovered that carefully drying the resistant starch to a moisture content of below 20% for example between 12-19% produced flowable starch that did not stick together. In other embodiments, the moisture content may be below 17%, for example, 12-17% or 12-15%.

Accordingly, in one embodiment of the invention, there is provided a method of preparing a resistant potato starch capsule comprising drying a quantity of resistant potato starch to below 20%, for example, below 17% and then flowing the dried resistant potato starch into a capsule. Specifically, the moisture content may be 12-19%, 12-17% or 12-15%.

The inventors also attempted to prepare resistant potato starch tablets as there were concerns that the resistant potato starch capsules may not have been the ideal delivery mechanism due to slow release of the starch from the capsule.

In these embodiments, solution of a suitable excipient is prepared and resistant starch is added to the solution. The mixture is then allowed to form into pellets or granules. The granules are dried and then reduced in size using any suitable means known in the art. The resistant potato starch material is formed into a tablet under a suitable pressure. Surprisingly, it was found that pressures typically used for tablet preparation, for example 200-500 MPa in the preparation of such tablets fractured the granule structure of the resistant starch, thereby greatly reducing the quantity of resistant starch in the tablet. Subsequent experimentation showed that pressures between 60-100 MPa is suitable to produce the tablet, while lower pressures produced tablets which broke apart and higher pressures fractured the granule structure of the resistant starch to an unacceptable degree.

In some embodiments, the excipient is a binder, for example, polyvinylpyrrolidone (PVP). Surprisingly, while other binders such as methylcellulose, gelatinized starch and hydroxypropylcelluose were tested, it was discovered that only PVP produced tablets having the desired properties.

In some embodiments, the pharmaceutical composition is prepared as follows: an aqueous solution of 1 part PVP is prepared. 9 parts resistant starch is dissolved therein at a temperature below 60° C. Pellets and granules are allowed to form which are then dried. The dried material is reduced in size with a hammer mill. The material is then formed into a tablet and subjected to a pressure between for example 45-100 MPa or in some preferred embodiments between 60-100 MPa.

As will be appreciated by one of skill in the art, the capsules and tablets may be made in any suitable size, for example, in a unit dosage to be taken once per day, or in dosages to be taken multiple times per day, for example twice or more per day on a suitable dosage regimen or schedule. For example, a suitable dosage regimen may be one or more capsules or tablets comprising 50-750 mg resistant potato starch prepared as discussed herein every 2, 4, 6, 8, 12 or 24 hours or taken with meals.

For example, the capsules or tablets may be 50 mg, 100 mg, 200 mg, 220 mg, 250 mg, 300 mg, 350 mg, 400 mg, 450 mg, 500 mg, 600 mg, 700 mg, 750 mg or any suitable similar size according to patient and/or consumer preference.

In some embodiments, each capsule may weigh 625±5.0 mg and each capsule may contain 528±17.6 mg of material of which 350-370 mg is resistant starch.

In some embodiments, the material is formed into tablets at a pressure between 45-100 MPa or between 60-100 MPa. In some embodiments, each tablet is 40-50% resistant starch, for example, 45% resistant starch.

In one embodiment of the invention, there is provided a method of preparing a resistant potato starch pharmaceutical composition comprising mixing an effective amount of resistant potato starch with a suitable excipient. The excipient may be PVP. The mixture may be 1 part or about 1 part PVP to 9 parts or about 9 parts resistant potato starch or resistant potato starch source. In some embodiments, the pharmaceutical composition is in the form of a tablet. In other embodiments, resistant potato starch is dried to a moisture content below 20% for example between 12-19% or below 17% for example between 12-17% and flowed into a suitably sized capsule, thereby producing a resistant potato starch capsule.

According to another embodiment of the invention, the pharmaceutical composition described above is used for treating infectious diarrhea in an animal.

According to another embodiment of the invention, the pharmaceutical composition described above is used for treating post-weaning diarrhea in an animal.

According to another embodiment of the invention, the pharmaceutical composition described above is used for treating gastrointestinal stresses associated with weaning in an animal.

In these embodiments, it is to be understood that the treatment may be prophylactic. That is, the resistant potato starch pharmaceutical composition may be administered to an animal for example a human at risk of developing or suspected of having infectious diarrhea, post-weaning diarrhea or stresses associated with weaning in an infant.

In these embodiments, it is to be understood that the pharmaceutical composition will be effective at treating or reducing the severity or frequency of occurrence of one or more symptoms associated with infectious diarrhea, post-weaning diarrhea or stresses associated with weaning compared to an untreated control or mock treated control of similar age, weight and condition. Symptoms include but are by no means limited to for example diarrhea, low fecal consistency, increased pH in the digestive tract, and increased levels of nitrogen-fixing bacteria.

According to one embodiment of the invention, there is provided a method of treating or preventing or prophylactically treating infectious diarrhea in an animal comprising administering to an animal in need of such treatment an effective amount of resistant potato starch.

According to one embodiment of the invention, there is provided a method of treating or preventing or prophylactically treating post-weaning diarrhea in an animal comprising administering to an animal in need of such treatment an effective amount of resistant potato starch.

As will be appreciated by one of skill in the art, infective diarrhea is typically caused by an infection with a gastrointestinal pathogen for example a virus or bacterial strain. The gastrointestinal pathogen can be transmitted to other animals infectiously. Accordingly, in these embodiments, the resistant potato starch may be administered to an animal having infective diarrhea, suspected of having infectious diarrhea or at risk of developing infectious diarrhea. This may be any animal in an environment in which there is risk of developing or encountering infectious diarrhea pathogens. The animal may be a human.

According to one embodiment of the invention, there is provided a method of treating or preventing or prophylactically treating gastrointestinal stresses associated with weaning in an animal comprising administering to an animal in need of such treatment an effective amount of resistant potato starch.

As will be readily apparent to one of skill in the art, "an effective amount" will depend on the animal, its age, weight and general condition, among other factors. However, as discussed above, the inventors have discovered that a much lower level of resistant starch than previously believed is sufficient to treat or otherwise ameliorate at least one of the symptoms associated with infectious diarrhea, post-weaning diarrhea and/or gastrointestinal stresses associated with weaning such as fecal consistency, daily food intake and the like. For example, in some embodiments, the "effective amount" is resistant starch at approximately 0.1%-2.5%, 0.1-2.0%, 0.1-1.5%, 0.1-1.0%, 0.2-2.5%, 0.2-2.0%, 0.2-1.5%, 0.2-1.0%, 0.3-2.5%. 0.3-2.0%, 0.3-1.5%, 0.3-1.0%, 0.4-2.5%. 0.4-2.0%, 0.4-1.5%, 0.4-1.0%, 0.5-2.5%. 0.5-2.0%, 0.5-1.5%, or 0.5-1.0% of the animal's diet.

In other embodiments, the "effective amount" may be a resistant starch capsule or tablet. The resistant starch capsule or tablet may be prepared according to the methods described herein. Preferably, the resistant starch capsule is a 500 mg capsule. The tablet may be a 220 mg tablet or a 250 mg tablet.

According to another embodiment of the invention, there is provided the use of resistant potato starch for treating infectious diarrhea in an animal.

According to another embodiment of the invention, there is provided the use of resistant potato starch for treating post-weaning diarrhea in an animal.

According to another embodiment of the invention, there is provided the use of resistant potato starch for treating gastrointestinal stresses associated with weaning in an animal.

In yet another embodiment of the invention, there is provided a transitional food product for weaning animals comprising an effective amount of resistant potato starch.

In the embodiments discussed above, the resistant potato starch is preferably naturally high in resistant starch, that is, at least 60-80% resistant starch. In yet more preferred embodiments, the resistant potato starch is MSPrebiotic® Resistant Starch (resistant potato starch for human health indications) or MSP[RS]® Resistant Starch (resistant potato starch for livestock industry use).

As will be appreciated by one of skill in the art, such a transitional food product may be a cereal or fruit or vegetable product processed and prepared for consumption by a post-weaning mammal such as a human infant supplemented with an effective amount of resistant starch.

In summary, the inventors have surprisingly discovered that contrary to the prevalent belief in the art, levels of resistant potato starch below 1.0% of a diet are sufficient and effective to treat post-weaning diarrhea. This is supported at least by Table 4, described below, which shows a decrease in branched chain fatty acids (BCFA) and an increase in volatile fatty acid (VFA) concentration in the cecum, regardless of the delivery format of the resistant potato starch, provided care is taken in the preparation of the resistant potato starch material such that fracturing of the resistant starch granule structure is minimized. This is significant, given concerns regarding the possibility of capsules having a slow release profile and also of the impact of pressure used during the formation of resistant potato starch tablets. As discussed above, the inventors have determined a window of suitable pressures which produce tablets having the desired properties in which a significant portion of the resistant starch is retained. Similarly, the inventors have discovered that less than 20% moisture is a critical threshold for obtaining flowable resistant potato starch for the preparation of capsules.

The study was conducted to evaluate the effect of feeding weaned pigs a resistant starch, in some embodiments, MSP [RS]® resistant starch on growth performance, fecal consistency and gastrointestinal tract (GIT) characteristics. Sixty piglets (Yorkshire×Large White×Duroc) weaned at 21 d (1:1 gender ratio) with an initial BW of 7.17±0.78 kg were assigned in a completely randomized design to one of five dietary treatments to give 6 observations per treatment (2 pigs per pen). Dietary treatments consisted of a negative control corn-soybean meal-based diet (NC; no antibiotic agents added) or the NC supplemented with resistant starch either as powder or in capsules and each included at 0.5 or 1.0%. Pigs were offered the experimental diets on an ad libitum basis for 4 weeks and water was available at all times. Body weight and feed intake were monitored weekly. At the end of week 4, 6 pigs per treatment (3 for each gender) were euthanized to collect digesta and organs. Resistant starch supplementation improved (P<0.001) fecal consistency, and 1.0% dose of resistant starch had more solid feces (P<0.05) compared with 0.5% of resistant starch during the first 2 weeks after weaning, independent of dosage form of resistant starch. Resistant starch supplementation decreased ileal and cecal digesta pH (P<0.05) compared with the NC. In addition, resistant starch supplementation tended to increase VFA concentrations but tended to decrease the molar proportion of BCFA in the cecum (P=0.073 and P=0.057, respectively), regardless of dosage form of resistant starch, compared with NC. However, there were no differences (P>0.05) in number of antibiotic treatments, ADG, ADFI, FCR and organ weights and intestinal $NH_3$—N among treatments. It was concluded that supplementing a nursery pig diet with at least 0.5% of resistant starch has potential to enhance outcomes characteristic of a health gut in weaned piglets.

The purpose of this study was to examine whether a lower supplementation level (i.e., 0.5 and 1.0%) of MSP [RS]® resistant starch to nursery pig diets without in-feed antibiotics would have comparable effects on PWD and physiological intestinal characteristics to those observed previously when piglets were fed a diet containing 7% RPS (Bhandari et al., 2009). Also, results of the study by Bhandari et al. (2009) including RPS at 14% in nursery pig diets might have adverse effects on gastrointestinal physiology. However, it is unknown as to whether including RPS in piglet diets at lower levels than 7% will still confer similar effects as seen with the 7% inclusion level. This is critical as a lower inclusion level will likely pose fewer challenges in diet formulation. Results of the current study indicate that supplementing a nursery pig diet containing no in-feed antimicrobials with at least 0.5% of resistant starch has potential to enhance outcomes characteristic of a health gut in weaned piglets.

Supplementing piglet diet with resistant starch improved fecal consistency, which is in agreement with previous reports (Callesen et al., 2007; Bhandari et al., 2009). These studies showed that around 7% of RPS supplementation in the diet reduced PWD without in-feed antibiotic. However, results of the current study seem to suggest that as low as 0.5% of resistant starch supplementation in the diet might offer an effective dietary strategy to minimize incidences of PWD. There was a strong trend towards a decreased BCFA (branched-chain fatty acids) concentration with resistant starch supplemented diets coupled with tendency towards an increase in VFA concentrations in the cecum. These observations have been implicated in the pathogenesis of PWD (Aumaitre et al., 1995; Williams et al., 2001; Pluske et al., 2002). Indeed, pigs fed resistant starch supplemented diets had lower pH in the ileum and cecum. This could be due to the fact that resistant starch supplementation increased the amount of substrate available for fermentation by carbohydrate utilizing gut microbiota. It is well documented that feeding fermentable carbohydrates can alter bacterial populations and their activity (Bauer et al., 2001; Hogberg et al., 2004; Metzler et al., 2009). However, resistant starch supplementation had no effect on ammonia nitrogen concentrations in the ileum and caecum.

No differences were found in growth performance and visceral organ weight in the current study among dietary treatments. This finding is in agreement with results of others (Kerr et al., 1998; Bhandari et al., 2009). This was most likely due to the fact that experimental diets were formulated to contain equivalent amounts of digestible energy content (DE), standardized ileal lysine/kg DE and crude protein level. It may also be due to the fact that the amount of supplemental resistant starch used in the current study was too low to have any negative effects on nutrient digestion and utilization.

In conclusion, the results of the present experiment demonstrated that at least 0.5% resistant starch without any in-feed antibiotic improved faecal consistency commensurate with reduced pH in the ileum and colon, but did not affect growth performance and visceral organ weight for 4 weeks after weaning.

Results

Piglets remained healthy and performed well throughout the study, although one pig in the negative control diet refused to consume experimental diet and was subsequently excluded from this study for all measurements.

Resistant starch supplementation improved (P<0.001) fecal consistency, and 1.0% dose of resistant starch had more solid feces (P<0.05) compared with 0.5% of resistant starch during the first 2 week after weaning, independent of dosage form of resistant starch (Table 2).

Resistant starch supplementation decreased ileal and cecal digesta pH (P<0.05) compared with the NC and also tended to increase VFA concentrations, but tended to decrease the molar proportion of BCFA in the cecum (P=0.073 and P=0.057, respectively), regardless of dosage form of resistant starch, compared with NC. However, there were no differences (P>0.05) in NH3-N concentration in the ileal and cecal contents among treatments (Tables 3 and 4).

As discussed above, the material used for this research was MSP [RS]® Resistant Starch.

The experimental protocol used in the present study was reviewed and approved by the Animal Care Committee of the University of Manitoba. Animals were cared for according to the guidelines of the Canadian Council on Animal Care (CCAC, 2009).

Animals, Housing and Experimental Design

A total of 60 piglets (Yorkshire×Large White×Duroc; initial BW of 7.17±0.78 kg) weaned at 21±2 days (1:1 gender ratio) were obtained from Glenlea Swine Research Station at the University of Manitoba and assigned to treatments in a completely randomized design. Pigs were weighed and assigned to outcome groups on the basis of BW and gender, and randomly allocated to 5 treatments, consisting of 2 pigs per pen, and 6 replicates. Each pen had a plastic-covered expended metal floor, a stainless-steel feeder, and a low-pressure nipple drinker. Pigs had unlimited access to feed and water throughout the 4-week study. The severity of diarrhea was scored using fecal consistency scoring system as developed by Heo et al. (2008) to investigate impact of resistant starch on post-weaning diarrhea for 2 weeks after weaning. Pigs were weighed once weekly for 4 weeks and feed disappearance was recorded on a pen basis each week and the two variables were used to calculate feed conversion ratio. Room temperature was maintained at 29±1° C. for the initial week, and then decreased by 2° C. in the second week. On day 28, six pigs per treatment balance for gender (n=30) were euthanized by an intracardiac injection of sodium pentobarbital (110 mg/kg BW), so as to collect intestinal digesta and organ.

Experimental Diets

Dietary treatments consisted of a negative control corn-soybean meal-based diet (NC; no antimicrobial agents added) or the NC supplemented with resistant starch either as powder or in capsules and each included at 0.5 or 1.0%. Experimental diets were formulated to meet or exceed NRC (1998) nutrient requirements for pigs weighing 7 to 20 kg. Pigs were fed phase-1 diets for the first 2 weeks and phase-II diets thereafter.

Digesta Sampling

At the end of the study, the pig with a BW closest to the mean pen BW was held under general anesthesia and killed by an intracardiac injection of sodium pentobarbital (50 mg/kg BW). Following euthanasia the abdominal cavity was opened from sternum to pubis to expose the gastrointestinal tract without damaging the wall of the digestive tract. The stomach, small intestine, and large intestine were weighed with and without digesta to determine digesta and empty weights, respectively. The liver, spleen and kidney were also weighed. The small intestine was stripped free of its mesentery and further divided into 3 sections: 1) the ileum from the ileal-cecal junction to 80-cm anterior to this junction; 2) the duodenum, 80 cm posterior to the gastro-duodenal sphincter; and 3) the jejunum constituted the regions between the ileum and duodenum (Bhandari et al., 2009). Digesta samples were taken from the ileum and cecum for measurement of pH, VFA, and ammonia N concentrations. The pH was determined immediately using a pH meter (AB 15, Fisher Scientific, Pittsburgh, Pa.) and samples were stored at −20° C. until analyzed for VFA and NH3- N concentrations.

Chemical Analyses

The DM was determined according to the AOAC (1990; method 925.09) and GE content was measured using an adiabatic bomb calorimeter (model 6300, Parr Instrument, Moline, Ill., USA) which had been calibrated using benzoic acid as a standard. Nitrogen (N) content was determined using the combustion method (990.03; AOAC, 1990) using the LECO (model CNS-2000; LECO Corp., St. Joseph, Mich., USA) N analyser.

Statistical Analyses

Treatment effects were evaluated univariatelyin a normal mixed-linear model using the GLM procedure of SPSS (version 18.0, SPSS Inc., Chicago, Ill., USA). The pen was the experimental unit for all measurements, and the model included treatment and gender as sources of variation. Since no gender effect was detected (P>0.05), data were pooled and analysed for treatment effects. Initial BW was included in the model as a covariate for analyses of growth performance data. The pig was the experimental unit for the fecal consistency and gastrointestinal characteristics. Statistical significance was accepted at P<0.05. Pair-wise comparisons between means were made when appropriate using Duncan's LSD analysis when a significant treatment effect was observed.

Preparation of Resistant Starch Tablets

Formulation: 90% resistant potato starch+10% PVP, the water should be 30% of the total amount of the flour. For example, 9 kg resistant potato starch plus 1 kg PVP, the water should be 10×30%=3 kg (3 liter).

Procedure

Step 1: Resistant Potato starch, PVP, and water are weighed respectively.

Step 2: Dissolve the PVP into water, heat and dissolve it.

Step 3: Cool down the PVP solution in ice water bath into room temperature.

Step 4: Add the PVP solution into Resistant Potato starch powders and mix thoroughly with a mixer (10-20 min depending on the amount).

Step 5: Screening the damp mass through a mesh to form pellets or granules with a granulator.

Step 6: Drying the granules by using a dryer in 40-45° C. for about 72 h, depending on the amount of the granules prepared.

Step 7: After the granules are dried, they are passed through a hammer mill (We use #4 screen, with 0.75 mm diameter holes).

Step 8: Go through the tablet machine (Pressure of 60-100 MPa is required for the resistant starch which contains 60-75% RS. Higher RS requires higher pressure. The final tablet product should contain about 40% RS, db).

While the preferred embodiments of the invention have been described above, it will be, recognized and understood that various modifications may be made therein, and the appended claims are intended to cover all such modifications which may fall within the spirit and scope of the invention.

Tables

TABLE 1

Composition of the experimental diets (%, as-fed basis)

| Item | Phase I | Phase II |
|---|---|---|
| Barley | | 14.00 |
| Corn | 20.7 | 9.95 |
| Wheat HRW | 16.80 | 37.00 |
| Millrun | — | 10.00 |
| Canola meal | 10.00 | — |
| SBM 44% | 20.00 | 20.00 |
| Fish meal | 6.79 | 3.55 |
| Dried Whey | 20.00 | — |
| Vegetable oil | 4.00 | 2.15 |
| Limestone | 0.40 | 0.90 |
| Monocalcium phosphorus | — | 0.71 |
| Vit-Min Premix[1] | 1.00 | 1.00 |
| Lys-HCl | 0.01 | 0.27 |
| Threonine | — | 0.10 |
| DL-Methionine | — | 0.07 |
| TiO$_2$ | 0.3 | 0.3 |
| Calculated nutrient content | | |
| DE, kcal/kg | 3,556 | 3,351 |
| CP, % | 23.00 | 20.00 |
| Ca, % | 0.801 | 0.762 |
| tP, % | 0.702 | 0.695 |
| Av. P, % | 0.435 | 0.417 |
| SID Lys, g/Mcal DE | 3.439 | 3.434 |

[1]Provided the following nutrients (per kg of air-dry diet): Vitamins: A, 8250 IU, D3, 825 IU, E, 40 mg, K, 4 mg, B1, 2 mg, B2, 10 mg, B6, 4.5 mg, B12, 25 μg, calcium pantothenate, 15 mg, folic acid, 2 mg, niacin, 22.5 mg, biotin, 200 μg. Minerals: Cu, 25 mg(as copper sulphate), iodine, 0.4 mg (as potassium iodine), iron, 100 mg (as ferrous sulphate), Mn, 50 mg (as manganous oxide), Se, 0.3 mg (as sodium selenite), Zn, 150 mg (as zinc oxide)

TABLE 2

Effect of resistant starch on fecal consistency in weaned pigs fed different experimental diets after weaning

| Item | Control | 0.5% Powder | 1.0% Powder | 0.5% Capsules | 1.0% Capsules | SEM | P-value |
|---|---|---|---|---|---|---|---|
| | | | Fecal consistency[1], % | | | | |
| Week 1 | 31.4 | 29.3 | 28.6 | 30.5 | 28.6 | 0.40 | 0.116 |
| Week 2 | 49.0$^c$ | 42.6$^b$ | 35.7$^a$ | 45.2$^{bc}$ | 32.0$^a$ | 0.66 | <0.001 |
| Week 1-2 | 40.2$^c$ | 36.0$^b$ | 32.1$^a$ | 37.9$^{bc}$ | 30.3$^a$ | 0.45 | <0.001 |

[1]Fecal consistency scoring [0 (0%), very hard; 1 (20%); well-formed feces; 2 (40%), soft-formed; 3 (60%), sloppy; 4 (80%), pasty diarrhea; 5 (100%), liquid diarrhea]

TABLE 3

Effect of resistant starch on intestinal pH in weaned pigs fed different experimental diets after weaning

| Item | Control | 0.5% Powder | 1.0% Powder | 0.5% Capsules | 1.0% Capsules | SEM | P-value |
|---|---|---|---|---|---|---|---|
| | | | pH | | | | |
| Stomach | 2.8 | 3.3 | 3.3 | 3.2 | 3.3 | 0.08 | 0.967 |
| Duodenum | 6.2 | 6.4 | 6.5 | 6.4 | 6.4 | 0.07 | 0.924 |
| Jejunum | 7.3 | 7.5 | 7.4 | 7.4 | 7.4 | 0.07 | 0.927 |
| Ileum | 7.7$^a$ | 7.4$^b$ | 7.3$^b$ | 7.3$^b$ | 7.2$^b$ | 0.03 | 0.002 |
| Caecum | 6.4$^a$ | 6.2$^b$ | 6.2$^b$ | 6.3$^b$ | 6.2$^b$ | 0.02 | <0.001 |
| Colon | 7.1 | 7.1 | 7.2 | 7.2 | 7.0 | 0.06 | 0.997 |

TABLE 4

Effect of resistant starch on intestinal VFA and $NH_3$—N in weaned pigs fed different experimental diets after weaning

| Item | Control | 0.5% Powder | 1.0% Powder | 0.5% Capsules | 1.0% Capsules | SEM | P-value |
|---|---|---|---|---|---|---|---|
| | | | Ileal VFA, mmol/kg | | | | |
| Total | 15 | 16 | 13 | 12 | 20 | 1.6 | 0.593 |
| BCFA[1], % | 4.3 | 5.8 | 5.0 | 5.2 | 3.7 | 0.40 | 0.510 |
| | | | Cecal VFA, mmol/kg | | | | |
| Total | 137 | 147 | 148 | 147 | 147 | 1.3 | 0.073 |
| BCFA, % | 4.4 | 2.7 | 2.2 | 2.9 | 2.6 | 0.24 | 0.057 |
| | | | NH3—N,mg/kg | | | | |
| Ileum | 32 | 25 | 25 | 25 | 24 | 1.5 | 0.435 |
| Cecum | 101 | 99 | 104 | 103 | 100 | 1.8 | 0.885 |

[1]Branched-chain fatty acids; molar proportion of isobutyic acid, isovaleric acids and valeric acid with respect to the total VFA. Valeric acid is considered to be associated with protein degradation from metabolism of AA (Macfarlane et al., 1992)

TABLE 5

Effect of resistant starch on visceral organ weight in weaned pigs fed different experimental diets after weaning

| Item | Control | 0.5% Powder | 1.0% Powder | 0.5% Capsules | 1.0% Capsules | SEM | P-value |
|---|---|---|---|---|---|---|---|
| | | | Organ weight, g/kg of BW | | | | |
| Stomach | 9.4 | 9.9 | 9.2 | 8.9 | 9.8 | 0.23 | 0.608 |
| SI[1] | 44.9 | 41.9 | 45.0 | 43.2 | 46.8 | 0.85 | 0.451 |
| Cecum | 3.2 | 3.5 | 2.9 | 3.4 | 3.2 | 0.09 | 0.226 |
| LI[1] | 22.4 | 22.6 | 23.7 | 22.6 | 23.4 | 0.49 | 0.893 |
| Liver | 32.6 | 34.0 | 33.8 | 32.7 | 35.1 | 0.58 | 0.633 |
| Spleen | 3.6 | 3.3 | 3.8 | 3.7 | 3.7 | 0.18 | 0.940 |
| Kidney | 6.1 | 6.1 | 6.5 | 6.3 | 6.5 | 0.11 | 0.641 |

[1]Abbreviations: SI, small intestine; LI, large intestine

TABLE 6

Effect of resistant starch on growth performance in weaned pigs fed different experimental diets after weaning

| Item | Control | 0.5% Powder | 1.0% Powder | 0.5% Capsules | 1.0% Capsules | SEM | P-value |
|---|---|---|---|---|---|---|---|
| ADG, g/d | | | | | | | |
| Week 1 | 66 | 83 | 81 | 77 | 79 | 6.8 | 0.939 |
| Week 2 | 310 | 313 | 328 | 308 | 281 | 10.1 | 0.782 |
| Week 3 | 305 | 265 | 312 | 336 | 288 | 9.9 | 0.225 |
| Week 4 | 407 | 418 | 372 | 431 | 349 | 11.6 | 0.168 |
| Week 1-4 | 272 | 270 | 273 | 288 | 257 | 5.8 | 0.597 |
| ADFI, g/d | | | | | | | |
| Week 1 | 165 | 188 | 182 | 187 | 189 | 6.3 | 0.735 |
| Week 2 | 408 | 497 | 467 | 469 | 497 | 17.1 | 0.472 |
| Week 3 | 608 | 541 | 561 | 594 | 491 | 16.2 | 0.220 |
| Week 4 | 776 | 741 | 747 | 788 | 665 | 19.4 | 0.366 |
| Week 1-4 | 489 | 492 | 489 | 509 | 461 | 8.2 | 0.508 |
| FCR, g/g | | | | | | | |
| Week 1 | 2.12 | 2.55 | 2.79 | 2.72 | 2.53 | 0.238 | 0.921 |
| Week 2 | 1.33 | 1.63 | 1.47 | 1.54 | 1.84 | 0.067 | 0.230 |
| Week 3 | 2.06 | 2.20 | 1.86 | 1.82 | 1.80 | 0.109 | 0.730 |
| Week 4 | 1.93 | 1.79 | 2.01 | 1.84 | 1.95 | 0.045 | 0.539 |
| Week 1-4 | 1.77 | 1.87 | 1.78 | 1.73 | 1.86 | 0.036 | 0.696 |

Abbreviations:
ADG, average daily gain;
ADFI, average daily feed intake;
FCR, feed conversion ratio

TABLE 7

Resistant starch content of a number of sample foods

| Food Sample | RS Content |
|---|---|
| Wheat Bran | 0.42 |
| Corn Flakes | 2.8 |
| Native potato starch | 78.1 |
| Cooked and cooled potato starch | 3.8 |

REFERENCES

AOAC, 1990. Official methods of Analysis of Analysis of AOAC International, 15th ed. Association of Official Analytical Chemists Washington, D.C.

Aumaitre, A., Peiniau, J., Madec, F., 1995. Digestive adaptation after weaning and nutritional consequences in the piglet. Pig News and Information 16, 73N-79N.

Bauer, E., Williams, B. A., Voigt, C., Mosenthin, R., Verstegen, M. W. A., 2001. Microbial activities of faeces from unweaned and adult pigs, in relation to selected fermentable carbohydrates. Animal Science 73, 313-322.

Bhandari, S. K., Nyachoti, C. M., Krause, D. O., 2009. Raw potato starch in weaned pig diets and its influence on postweaning scours and the molecular microbial ecology of the digestive tract. Journal of Animal Science 87, 984-993.

Callesen, J., Halas, D., Thorup, F., Knudsen, K. E. B., Kim, J. C., Mullan, B. P., Hampson, D. J., Wilson, R. H., Pluske, J. R., 2007. The effects of weaning age, diet composition, and categorisation of creep feed intake by piglets on diarrhoea and performance after weaning. Livestock Science 108, 120-123.

CCAC, 2009. Guidelines on the care and use of farm animals in research, teaching and testing. Canadian Council on Animal Care, Ottawa.

Gibson, G. R., Probert, H. M., Loo, J. V., Rastall, R. A., Roberfroid, M. B., 2004. Dietary modulation of the human colonic microbiota: updating the concept of prebiotics. Nutrition Research Reviews 17, 259-275.

Heo, J. M., Kim, J. C., Hansen, C. F., Mullan, B. P., Hampson, D. J., Pluske, J. R., 2008. Effects of feeding low protein diets to piglets on plasma urea nitrogen, faecal ammonia nitrogen, the incidence of diarrhoea and performance after weaning. Archives of Animal Nutrition 62, 343-358.

Heo, J. M., Opapeju, F. O., Pluske, J. R., Kim, J. C., Hampson, D. J., Nyachoti, C. M., 2012. Gastrointestinal health and function in weaned pigs: A review of feeding strategies to control post-weaning diarrhoea without using in-feed antimicrobial compounds. Journal of Animal Physiology and Animal Nutrition.

Hogberg, A., Lindberg, J. E., Leser, T., Wallgren, P., 2004. Influence of cereal non-starch polysaccharides on ileo-caecal and rectal microbial populations in growing pigs. Acta Veterinaria Scandinavica 45, 87-98.

Kerr, C. A., Goodband, R. D., Tokach, M. D., Nelssen, J. L., Dritz, S. S., Richert, B. T., Bergstrom, J. R., 1998. Evaluation of enzymatically modified potato starches in diets for weanling pigs. Journal of Animal Science 76, 2838-2844.

Kim, J. C., Hansen, C. F., Mullan, B. P., Pluske, J. R., 2012. Nutrition and pathology of weaner pigs: Nutritional strategies to support barrier function in the gastrointestinal tract. Animal Feed Science and Technology 173, 3-16.

Lusk, J., L., F. B. N., Pruitt, J. R., 2006. Consumer demand for a ban on antibiotic drug use in pork production. American Journal of Agricultural Economics 88, 1015-1033.

Macfarlane, G. T., Gibson, G. R., Beatty, E., Cummings, J. H., 1992. Estimation of short-chain fatty acid production from protein by human intestinal bacteria based on branched-chain fatty acid measurements. FEMS Microbiology Ecology 101 81-88.

Metzler, B. U., Vahjen, W., Baumgärtel, T., Rodehutscord, M., Mosenthin, R., 2009. Changes in bacterial populations in the ileum of pigs fed low-phosphorus diets supplemented with different sources of fermentable carbohydrates. Animal Feed Science and Technology 148, 69-89.

NRC, 1998. Nutrient requirements of swine. National Academy Press, Washington, D.C.

Pluske, J. R., Pethick, D. W., Hopwood, D. E., Hampson, D. J., 2002. Nutritional influences on some major enteric bacterial diseases of pigs. Nutrition Research Reviews 15, 333-371.

Williams, B. A., Verstegen, M. W. A., Tamminga, S., 2001. Fermentation in the large intestine of single-stomached animals and its relationship to animal health. Nutrition Research Reviews 14, 207-227

The invention claimed is:

1. A method of treating or preventing or prophylactically treating gastrointestinal stresses associated with weaning in an animal comprising administering to a weaning animal having gastrointestinal stresses associated with weaning an effective amount of resistant potato starch, wherein the effective amount is 0.1-2.5% (weight percent) of the weaning animal's diet.

2. The method according to claim 1 wherein the effective amount is 0.3-2.5% of the animal's diet.

3. The method according to claim 1 wherein the resistant potato starch is administered as a resistant starch capsule or tablet.

4. The method according to claim 3 wherein the capsule or tablet is in a 500 mg form.

5. The method according to claim 1 wherein the animal is a livestock animal.

6. The method according to claim 1 wherein the animal is a weaning piglet.

7. The method according to claim 1 wherein the effective amount is 0.5-2.5% of the weaning animal's diet.

8. The method according to claim 1 wherein the effective amount is 0.5-2.0% of the weaning animal's diet.

9. The method according to claim 1 wherein the effective amount is 0.5-1.0% of the weaning animal's diet.

10. The method according to claim 1 wherein the gastrointestinal stress is post-weaning diarrhea.

11. The method according to claim 1 wherein the resistant potato starch is administered as a transitional food product for weaning animals.

12. The method according to claim 11 wherein the transitional food product is a cereal or fruit or vegetable product processed and prepared for consumption by a post-weaning mammal.

13. The method according to claim 12 wherein the mammal is a human infant.

14. The method according to claim 1 wherein the resistant potato starch is 60-80% resistant starch.

* * * * *